United States Patent [19]
Avallone

[11] Patent Number: 5,919,182
[45] Date of Patent: Jul. 6, 1999

[54] MEDICAL FLUID TRANSFER AND DELIVERY DEVICE

[75] Inventor: John M. Avallone, Providence, R.I.

[73] Assignee: Becton, Dickinson and Company, Franklin Lakes, N.J.

[21] Appl. No.: 08/928,271

[22] Filed: Sep. 12, 1997

[51] Int. Cl.$^6$ .................................................. A61B 19/00
[52] U.S. Cl. .............................. 604/411; 604/263; 141/27
[58] Field of Search ........................... 604/411–414, 403, 604/905, 263, 523, 192; 141/25, 27, 329, 330

[56] References Cited

U.S. PATENT DOCUMENTS

| | | | |
|---|---|---|---|
| 5,609,584 | 3/1997 | Gettig et al. ......................... | 604/905 X |
| 5,807,374 | 9/1998 | Caizza et al. ............................ | 604/411 |
| 5,820,621 | 10/1998 | Yale et al. ............................... | 604/411 |
| 5,832,971 | 11/1998 | Yale et al. ............................ | 604/414 X |

*Primary Examiner*—John D. Yasko
*Attorney, Agent, or Firm*—Arthur D. Dawson

[57] ABSTRACT

A fluid transfer device for accessing fluid from vials and ampoules includes a cannula assembly. The cannula assembly includes a hub. The fluid transfer device further includes a filling straw with a proximal end, a distal end and a passageway therethrough and a housing with an outside surface fixedly attached to the proximal end of the straw. The housing has a cavity therein to receive at least a portion of the cannula assembly. The housing has at least one flexible arm attached to the housing at an inboard end, with the arm projecting and being biased outwardly from the housing. The arms each have an outboard end with a lug thereon. The fluid transfer device of the invention also has a removable shield. The invention indcludes a shield with a sidewall that has at least one elongate open slot from the open proximal end and an opening in alignment with and spaced distally to the slot. The shield is disposed so that the filling straw and at least a portion of the housing is within the shield. The shield has an unlatched positioned wherein the shield is removable from the housing to expose the filling straw for use, and a latched position wherein the shield and the housing are locked together to form a unitary structure. The shield and the housing are locked together by replacement of the shield onto said housing so that the arm is within the slot and the lug engages the hole.

16 Claims, 4 Drawing Sheets

MEDICAL FLUID TRANSFER AND DELIVERY DEVICE

FIELD OF INVENTION

The invention is generally related to a device mountable on a hypodermic syringe or other medical fluid handling device. More particularly, the invention allows a practitioner to access an injectable liquid medicament contained in ampoules or vials with elastomeric closures to fill the syringe with the liquid medicament for subsequent delivery to a patient.

BACKGROUND

Liquid injectable medicaments are often stored in sealed ampoules with a frangible seal or vials with elastomeric closures. Practitioners generally access the ampoules by breaking the seal, and withdrawing the liquid through a conventional hypodermic needle into a syringe. When the medicament container is a vial with an elastomeric closure, the practitioner generally uses a conventional sharp hypodermic needle on a syringe to penetrate the closure and withdraws the medicament into the syringe. Conventionally, the filled syringe with the hypodermic needle is then used to administer the medicament directly to the patient, or to penetrate a septum on an intravenous (I.V.) set and deliver the medicament to the patient through a catheter. With the wide recognition of the hazards of blood borne pathogens by the medical community, device manufacturers have developed alternatives to conventional hypodermic needles for transferring medicaments from sealed vials and administering the medicaments to patients. Alternative transfer devices include the needleless I.V. sets that incorporate pre-slit septa that are accessible by a blunt cannula. These blunt cannula/pre-slit systems are widely available from several manufacturers. While the blunt cannula/slit septum system is very useful for transfer of a medicament from an already filled syringe into an I.V. delivery system, the problem of filling the syringe from a sealed ampoule or a vial with an elastomeric closure is not solved by the pre-slit septum/blunt cannula system.

Many commonly used medicaments are supplied lyophilized and are reconstituted under sterile conditions just prior to usage. These lyophilized materials are generally supplied sterile in air-tight containers that either have a frangible seal or a monolithic elastomeric closure to protect the contents from moisture, microbial contamination, and in some cases, oxygen. These same type containers are also commonly used for aqueous solutions of medicaments. Ampoules with frangible seals and vials with monolithic elastomeric closures are not easily accessible by blunt cannula devices. As a result, device manufacturers developed filling devices known as "filling straws" or "filling spikes". These devices are somewhat similar in appearance to hypodermic needles, but have a larger diameter and bulky appearance indicative of their intended usage, i.e., puncturing of septa, not patient's tissue. The filling straws generally have a sharpened beveled point at their distal ends, but the bevel shape is generally designed to penetrate septa without coring, rather than being designed to penetrate tissue. Ampoules are generally made of glass with a weakened area that allows the practitioner to break off the top and provide access to the ampoule's contents. The filling straws are generally mounted on a syringe and have a small enough diameter and sufficient length to be used to reach into an opened ampoule and withdraw the contents. When the filling straws are used on a vial with an elastomeric closure, the beveled point is used to penetrate the closure and provide access to the contents. Since the filling straws are designed to penetrate septa and generally present a too "formidable" appearance to be used for patient's tissue penetration, they generally are used as intended by the manufacturer. A practitioner may use a filling straw to withdraw a medicament into a syringe and then remove the filling straw and attach the syringe directly to an I.V. set by utilizing a P.R.N. adapter. (P.R.N. is an acronym for the Latin term pro re nata, literally translated "as the need arises".) Alternatively, a practitioner may choose to remove the filling straw and attach a blunt cannula to the syringe, then access the I.V. set through a pre-slit septum. These alternatives generally eliminate the need for sharp hypodermic needles, but according to most hospital sharps usage protocols, the sharpened filling spike is still treated as a sharp and requires special handling and disposition.

Device manufacturers strive to simplify the usage of filling and transfer devices for practitioners. Filling straws that incorporate a blunt cannula are available. These devices have a filling straw with a distal void that accepts a blunt cannula with a shield over the filling straw. When a practitioner uses such a combination device by removing the shield, either the filling straw or the blunt cannula may be inadvertently exposed. If a device was available that prevented inadvertent exposure of the sharpened filling straw, the art of filling syringes and transfer of liquid medicaments would be advanced. Such a device is described hereinbelow.

SUMMARY

A fluid transfer device of the present invention useful for accessing fluid from vials and ampoules includes a cannula assembly and including a cannula having a proximal end, a distal end and a lumen defining an axis therethrough. The cannula assembly has a hub fixedly attached to the proximal end of the cannula that has an open proximal end in fluid communication with the lumen. The fluid transfer device further includes a filling straw with a proximal end, a distal end and a passageway therethrough and a housing with an outside surface fixedly attached to the proximal end of the straw. The housing has a cavity therein to coaxially receive at least a portion of the cannula assembly to form a fluid path between the open proximal end of the hub and the distal end of the filling straw. The housing has at least one flexible arm attached to the housing at an inboard end, with the arm projecting and being biased outwardly from the housing. The arms each have an outboard end with a lug thereon. The fluid transfer device of the invention also has a removable shield with an open proximal end, a distal end and a sidewall that defines a receptacle therein. The sidewall of the shield also has at least one elongate open slot extending from the open proximal end, the sidewall also has a opening in alignment with and spaced distally from the slot. The shield is disposed so that the filling straw and at least a portion of the housing is within the receptacle. The shield has an unlatched positioned wherein the shield is removable from the housing to expose the filling straw for use, and a latched position wherein the shield and the housing are locked together to form a unitary structure. The unitary structure being removable from the hub to expose the cannula. The shield and the housing are locked together to form the unitary structure by overcoming the outward bias of the arm with the shield removed from the housing and replacement of the shield onto the housing so that the arm is substantially within the slot and the lug engages the opening, thereby locking the shield to the housing.

DETAILED DESCRIPTION

Figure 1:
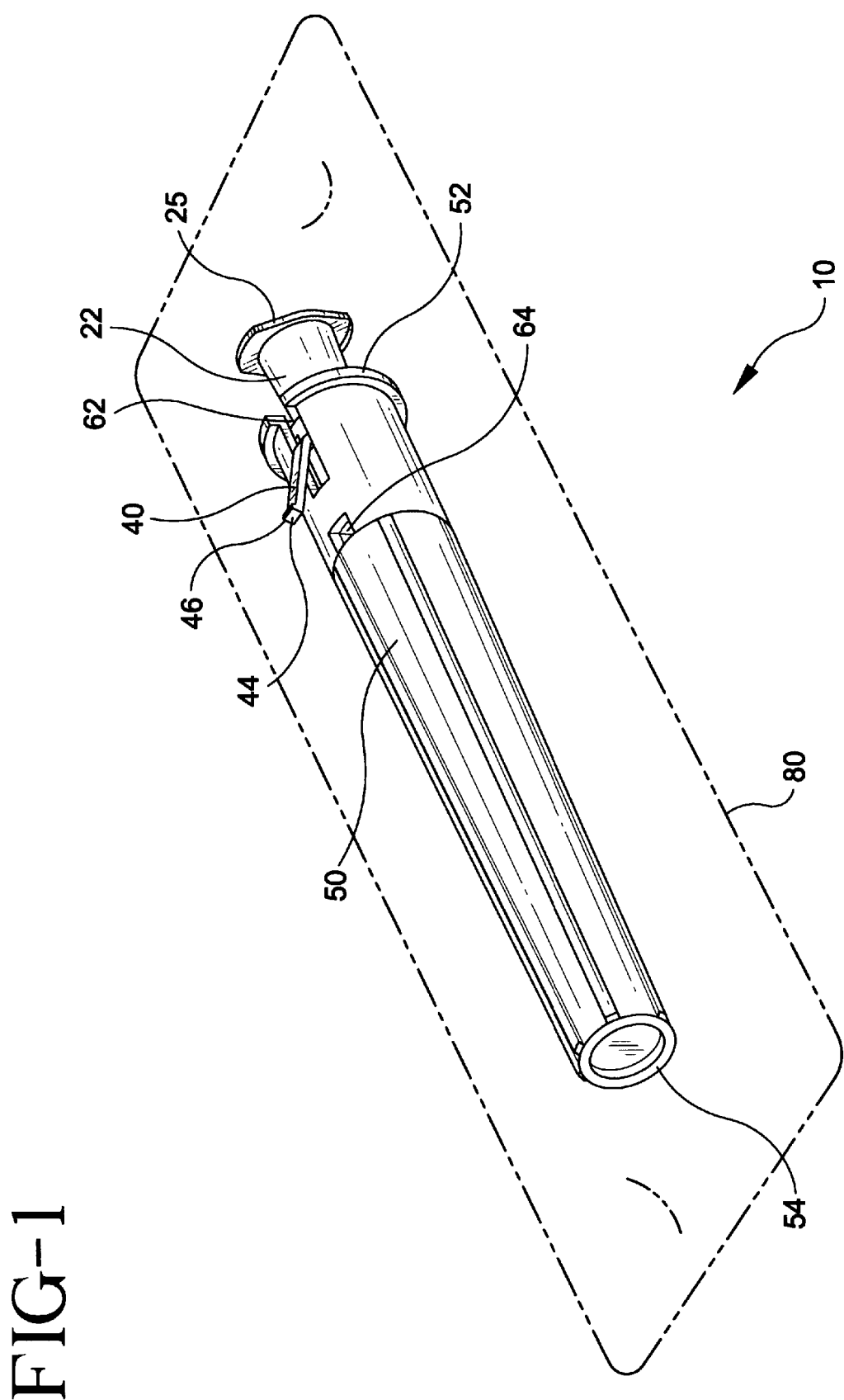
FIG. 1 is a perspective view of the fluid transfer device of the invention.

While this invention is satisfied by embodiments in many different forms, there are shown in the drawings and herein described in detail, embodiments of the invention with the understanding that the present disclosure is to be considered as exemplary of the principles of the present invention and is not intended to limit the scope of the invention to the embodiments illustrated. The scope of the invention is measured by the appended claims and their equivalents. For the purpose of this disclosure, the term "proximal" refers to the portion of the invention closest to the practitioner and the term "distal" refers to the portion of the device closest to the patient.

Referring to FIGS. 1–5, a fluid transfer device 10 of the present invention useful for accessing fluid from vials and ampoules includes a cannula assembly 12 that defines an axis "A" and includes a cannula 14 having a proximal end 16, a distal end 18 and a lumen 20 therethrough. Cannula assembly 12 has a hub 22 fixedly attached to proximal end 16 of cannula 14 that has an open proximal end 24 in fluid communication with lumen 20. Fluid transfer device 10 further includes a filling straw 26 with a proximal end 28, a distal end 30 and a passageway 32 therethrough. Filling straw 26 has a housing 34 with an outside surface 36 fixedly attached to proximal end 28 of the straw. Housing 34 has a cavity 38 therein to receive at least a portion of the cannula assembly 12 to form a fluid path between open proximal end 24 of hub 22 and distal end 18 of filling straw 26. Housing 34 has at least one flexible arm 40 attached to housing 34 at an inboard end 42, with arm 40 projecting and being biased outwardly from housing 34. Arms 40 each have an outboard end 44 with a lug 46 thereon. Fluid transfer device 10 also has a removable shield 50 with an open proximal end 52, a preferably closed distal end 54 and a sidewall 56 that defines a receptacle 60 therein. Sidewall 56 of shield 50 also has at least one elongate open slot 62 extending distally from open In, proximal end 52, and also has a opening 64 in alignment with and spaced distally to slot 62. Shield 50 is disposed so that filling straw 26 and at least a portion of housing 34 is within receptacle 60. Shield 50 has an unlatched positioned, best seen in FIG. 3, wherein shield 50 is removable from housing 34 to expose filling straw 26 for use. Shield 50 also has a latched position, best seen in FIG. 5, wherein shield 50 and housing 34 are locked together to form a unitary structure 66. Unitary structure 66 is removable from hub 22 to expose cannula assembly 12. Shield 50 and housing 34 are locked together to form unitary structure 66 by the practitioner overcoming the outward bias of arm 40 while shield 50 is removed from housing 34. The practitioner then replaces of shield 50 onto housing 34 so that arm 40 is substantially within slot 62 and lug 46 engages opening 64, thereby locking shield 50 to housing 34. Any subsequent removal of the shield then exposes only cannula assembly 12.

Preferably, housing 34 includes two arms 40 projecting at 180° apart outwardly therefrom and shield 50 has two slots 62 with aligned openings 64 disposed to engage arms 40.

Figure 2:
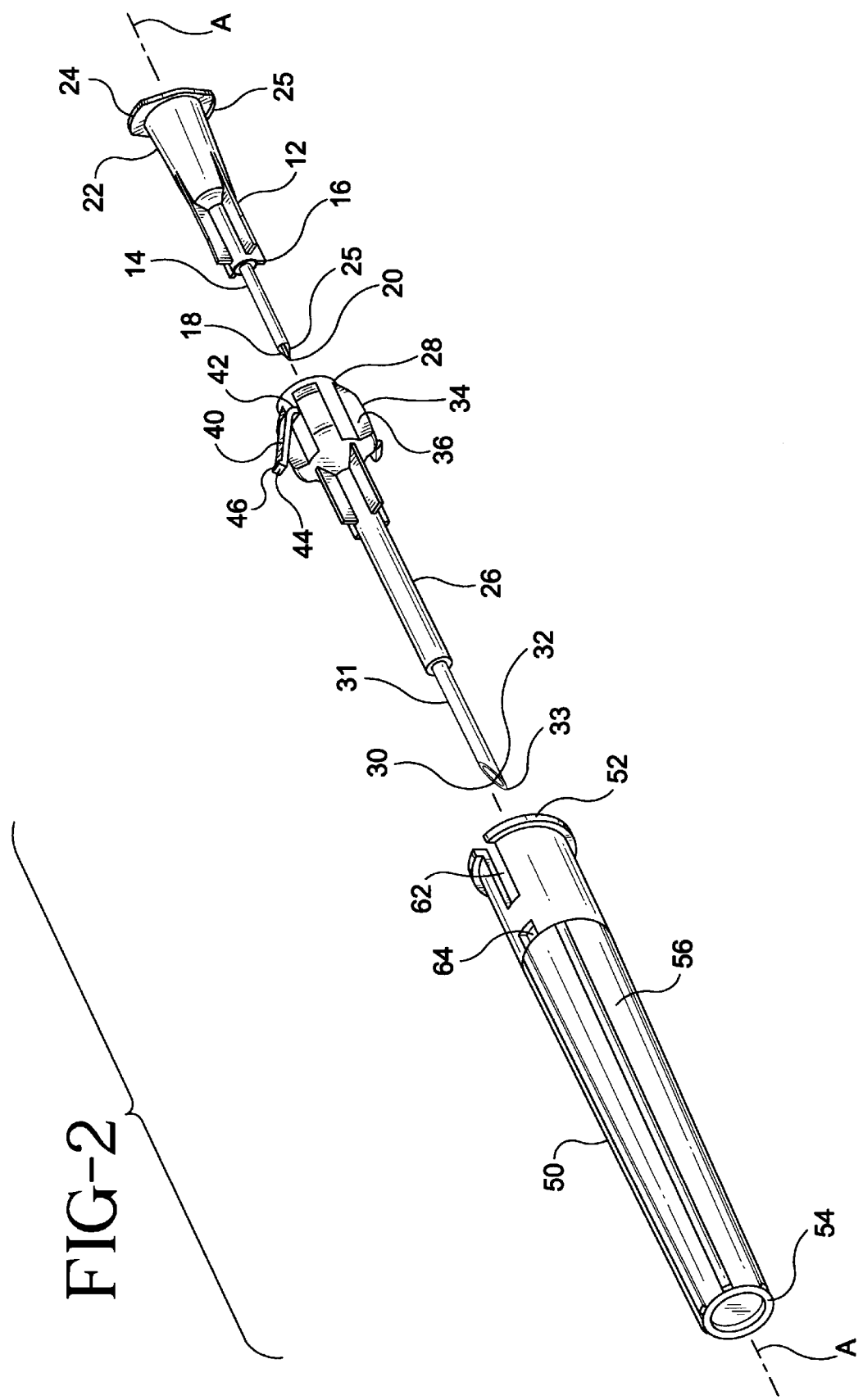
FIG. 2 is an exploded perspective view of the invention of FIG. 1.

Referring to FIG. 2, filling straw 26 has a distal portion 31 that may be formed from stainless steel. Alternatively, distal portion 31 may be integrally formed as a single article of manufacture with housing 34 from a thermoplastic material. Suitable thermoplastic materials include, but are not limited to, polyethylene, polypropylene, polycarbonate, acrylonitrile/butadiene/styrene (ABS), polyamide, polyacetal, copolymers of these thermoplastic materials and the like.

Preferably distal end 30 of the filling straw is formed with a sharpened surface 33 that describes a beveled surface with axis A to facilitate penetration of filling straw 26 through resilient stoppers of parenteral vials.

Figure 3:
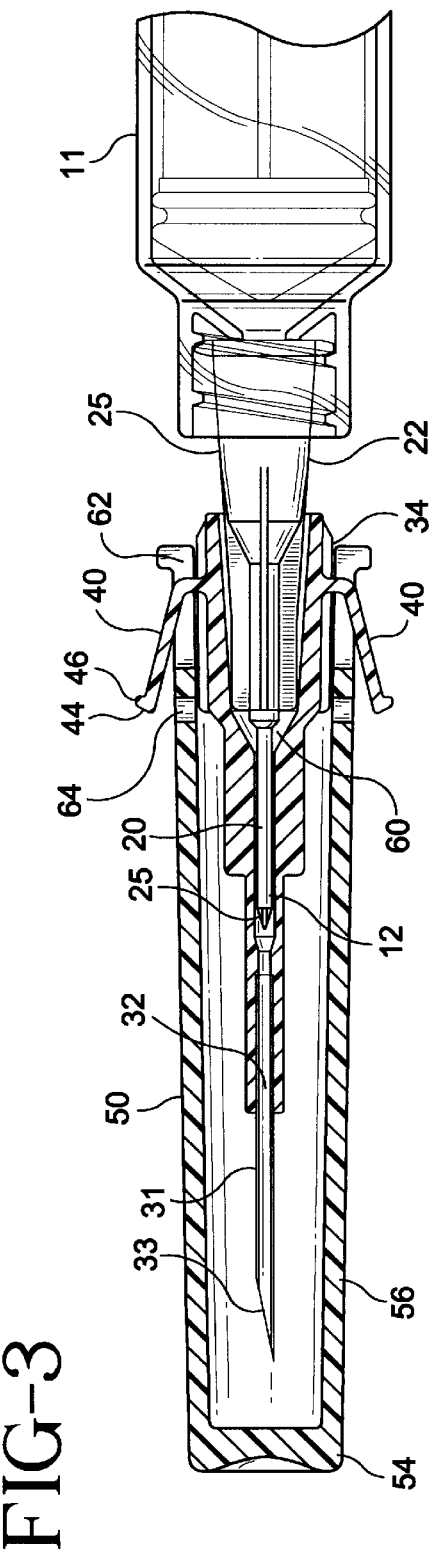
FIG. 3 is a longitudinal cross-sectional view of the invention of FIG. 1 mounted on a fluid handling device.
Figure 4:
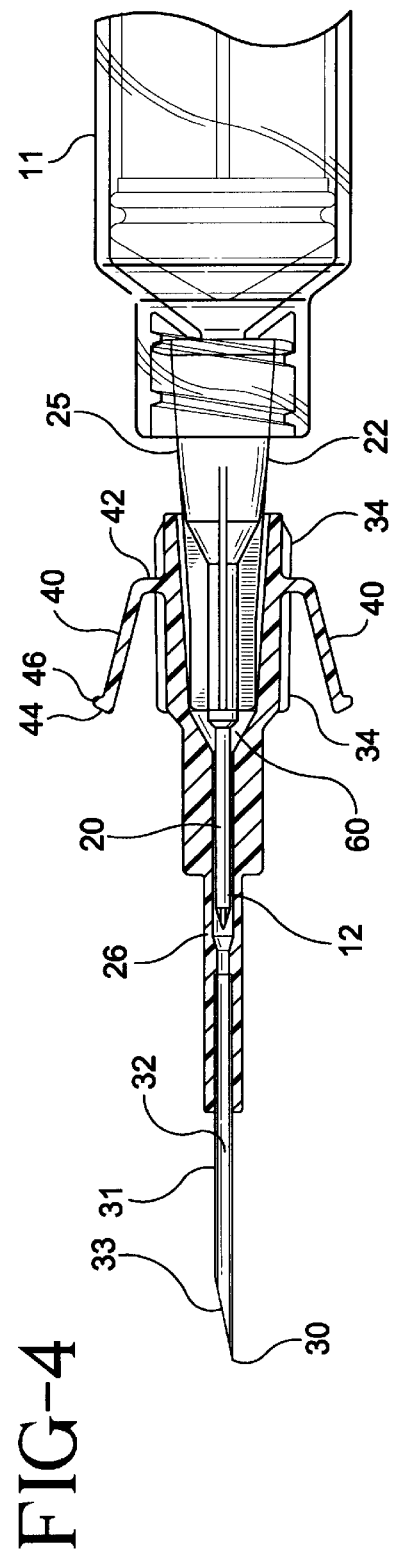
FIG. 4 is a longitudinal cross-section view of the invention of FIG. 1, analogous to FIG. 3, with the shield removed.
Figure 5:
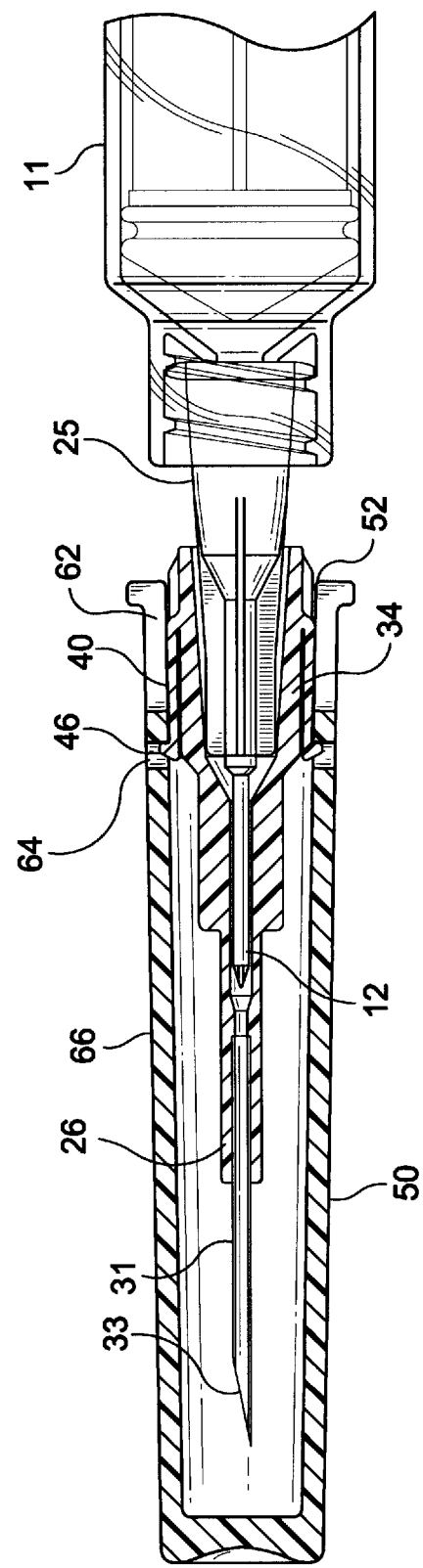
FIG. 5 is a longitudinal cross-section view of the invention of FIG. 1 with the shield replaced with the latch engaged.

Preferably, as shown in the FIGS. 3–5, hub 22 of the cannula assembly has a female luer fitting 25 at open proximal end 24 to facilitate attachment of fluid transfer device 10 to a syringe 11 or other fluid handling devices that have male luer fittings. As shown in FIG. 2, distal end 18 of cannula 14 preferably comprises a blunt rounded point 15. Cannula assembly 12 including cannula 14 and hub 22 is preferably formed as a single article of manufacture from a thermoplastic material such as polyethylene, polypropylene, polycarbonate, acrylonitrile/butadiene/styrene (ABS), polyamide, polyacetal, copolymers of these thermoplastic materials and the like.

As shown in phantom in FIG. 1, fluid transfer device 10 preferably is sealed in a package 80 that is formed from materials substantially resistant to the passage of microorganism and exposed to conditions that render any microorganisms inside package 80 substantially non-viable. Suitable materials for forming package 80 include, but are not limited to, paper, polymeric film, composites of paper and polymeric films, spun-bonded non-wovens and combinations of these materials. Suitable conditions for rendering microorganisms substantially non-viable include, but are not limited to, chemical sterilant agents such as ethylene oxide, gaseous hydrogen peroxide and the like as well as ionizing radiation such as is produced by $CO^{60}$, electron beam and the like. Consideration of the sterilization method should be made when selection of materials for forming device 10 and package 80 are made to ensure that the materials selected compatible with the sterilization conditions. When subjected to a validated sterilization in package 80, device 10 may be considered sterile as long as the package is intact.

A preferred method for filling a fluid handling device such as from a liquid medicament vial with a resilient closure with device 10 includes removing shield 50 to expose filling straw 26. Filling straw 26 with preferred sharp distal point 33 is then used to penetrate the resilient vial closure and allow the practitioner to withdraw the desired volume of liquid medicament into the syringe. The practitioner then depresses arms 40 against housing 34 and replaces shield 50 onto the housing with arms 40 within slots 62 so that lugs 46 engage opening 64. Shield 50 then covers the used filling straw and is latched to housing 34 to form unitary structure 66. Engagement of 40 arms with the openings 64 substantially prevents inadvertent access to filling straw 26 with sharp distal point 33. When the fluid handling device with the liquid medicament therein is delivered to the administration location, the practitioner then removes the now unitary structure 66 to expose the cannula assembly 12 to administer the medicament to the patient, When cannula 12 includes preferred blunt rounded point 25, the cannula is generally used with a pre-slit septum.

When fluid transfer device 10 is used with a syringe, the device allows a practitioner to selectively expose a filling straw to withdraw fluid from an ampoule or a vial with a resilient closure, then replace the shield and selectively lock it onto the housing. Subsequent removals of the shield only expose the cannula assembly for delivery of the dosage. As was described above, in many hospital dosage administration protocols, the dosages are often prepared at locations, such as a pharmacy, that are remote from the location where the dosage is actually administered to the patient. Many parenterals are available in unit dose ampoules or in multi-dose vials with resilient closures that require an elongate penetrating element to access the drug. Previously, the pharmacy would simply have used a conventional hypodermic needle both for filling the syringe and delivery directly into the patient, into a catheter or a delivery reservoir. With the recognition of the hazards of blood borne pathogens, many medication delivery protocols now specify elimination of sharp hypodermic needles and the use of a blunt cannula to introduce a parenteral medicament into a catheter or a delivery reservoir. However, practitioners still often need to make a penetration of a vial septum to fill a syringe. The device of the invention allows a practitioner to fill a syringe with a penetrating element and then provides a blunt cannula for the ultimate delivery without requiring the practitioner to remove the filling straw and replace it with a blunt cannula for administration. The fluid transfer device of the invention is simple to use and simplifies the hospital pharmacy practitioners' protocols and inventory.

What is claimed is:

1. A fluid transfer device for accessing fluid from vials and ampoules comprising:

a cannula assembly and including a cannula having a proximal end, a distal end and a lumen therethrough defining an axis, a hub fixedly attached to said proximal end of said cannula having an open proximal in fluid communication with said lumen;

a filling straw having a proximal end, a distal end and a passageway therethrough, a housing with an outside surface fixedly attached to said proximal end of said straw, said housing having a cavity therein to coaxially receive at least a portion of said cannula assembly to form a fluid path between said open proximal end of said hub and said distal end of said filling straw, said housing having at least one flexible arm attached to said housing at an inboard end, said arm projecting and being biased outwardly from said housing, said arm each having an outboard end with a lug thereon;

a removable shield having an open proximal end, a distal end and a sidewall defining a receptacle therein, said sidewall of said shield having at least one open slot extending from said open proximal end, each slot with an opening in alignment with and spaced distally from said slot, said shield being disposed so that said filling straw and at least a portion of said housing is within said receptacle, said shield having an unlatched positioned wherein said shield is removable from said housing to expose said filling straw for use, and a latched position wherein said shield and said housing are locked together to form a unitary structure, said unitary structure being removable from said hub to expose said cannula; and wherein said shield and said housing are locked together to form said unitary structure by overcoming said outward bias of said arm with said shield removed from said housing and replacement of said shield onto said housing so that said arm is substantially within said slot and said lug engages said opening, thereby locking said shield to said housing.

2. The fluid transfer device of claim 1 wherein said housing has two arms projecting outwardly therefrom and said shield has two slots with said aligned openings disposed to engage said arms.

3. The fluid transfer device of claim 2 wherein said arms are disposed 180° apart on said housing.

4. The fluid transfer device of claim 1 wherein said distal end of said shield is closed.

5. The fluid transfer device of claim 1 wherein said distal end of said cannula comprises a blunt rounded point.

6. The fluid transfer device of claim 1 wherein said distal end of said hub further comprises a female luer fitting.

7. The fluid transfer device of claim 1 wherein said distal end of said filling straw further comprises a sharpened surface that describes a bevel with said axis.

8. The fluid transfer device of claim 1 wherein said filling straw further comprises a distal portion with said housing being formed from a thermoplastic material.

9. The fluid transfer device of claim 8 wherein said filling straw distal portion is formed from stainless steel.

10. The fluid transfer device of claim 8 wherein said filling straw distal portion further comprises said distal end forming a bevel with said axis.

11. The fluid transfer device of claim 8 wherein said filling straw distal portion and said housing are formed as a single article of manufacture from a thermoplastic material.

12. The fluid transfer device of claim 11 wherein said thermoplastic material is selected from the group consisting of polyethylene, polypropylene, polycarbonate, acrylonitrile/butadiene/styrene (ABS), polyamide, polyacetal and copolymers thereof.

13. The fluid transfer device of claim 1 wherein said cannula and said hub are formed as a single article of manufacture from a thermoplastic material.

14. The fluid transfer device of claim 13 wherein said thermoplastic material is selected from the group consisting of polyethylene, polypropylene, polycarbonate, acrylonitrile/butadiene/styrene (ABS), polyamide, polyacetal and copolymers thereof.

15. The fluid transfer device of claim 1 wherein said device is sealed in a package formed from materials resistant to the passage of microorganisms and exposed to conditions rendering any microorganisms in said package non-viable.

16. A fluid transfer device for accessing fluid from vials and ampoules comprising:

a cannula assembly defining an axis and including a cannula having a proximal end, a distal end and a lumen therethrough, a hub fixedly attached to said proximal end of said cannula having an open proximal with a female luer fitting in fluid communication with said lumen;

a filling straw having a proximal end, a distal end and a passageway therethrough, a housing with an outside surface fixedly attached to said proximal end of said straw, said housing having a cavity therein to coaxially receive at least a portion of said cannula assembly to form a fluid path between said open proximal end of said hub and said distal end of said filling straw, said housing having two flexible arms attached to said housing at an inboard end, said arms being disposed 180° apart on said housing, said arms projecting and being biased outwardly from said housing and said arms each having an outboard end with a lug thereon;

a removable shield having an open proximal end, a distal end and a sidewall defining a receptacle therein, said sidewall of said shield having two open slots from said open proximal end disposed 180° apart, each slot with a opening in alignment with and spaced distal to said slot, said shield being disposed so that said filling straw and at least a portion of said housing is within said receptacle, said shield having an unlatched positioned wherein said shield is removable from said housing to expose said filling straw for use, and a latched position wherein said shield and said housing are locked together to form a unitary structure, said unitary structure being removable from said hub to expose said cannula; and wherein said shield and said housing are locked together to form said unitary structure by overcoming said outward bias of said arms with said shield removed from said housing and replacement of said shield onto said housing so that said arms are substantially within said slots and said lugs engage said holes, thereby locking said shield to said housing.

\* \* \* \* \*